US012265031B2

United States Patent
McElroy et al.

(10) Patent No.: US 12,265,031 B2
(45) Date of Patent: *Apr. 1, 2025

(54) SYSTEMS AND METHODS FOR THE DETECTION AND ANALYSIS OF FREE THIOL

(71) Applicant: ProteinSimple, San Jose, CA (US)

(72) Inventors: James McElroy, San Jose, CA (US); Christopher Heger, Campbell, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/604,002

(22) Filed: Mar. 13, 2024

(65) Prior Publication Data

US 2024/0344982 A1 Oct. 17, 2024

Related U.S. Application Data

(63) Continuation of application No. 17/181,610, filed on Feb. 22, 2021, now Pat. No. 11,953,436, which is a
(Continued)

(51) Int. Cl.
*G01N 33/68* (2006.01)
*A01N 1/02* (2006.01)
(Continued)

(52) U.S. Cl.
CPC ....... *G01N 21/6428* (2013.01); *G01N 33/582* (2013.01); *G01N 2440/20* (2013.01); *G01N 2500/00* (2013.01)

(58) Field of Classification Search
CPC ............ G01N 21/6428; G01N 33/582; G01N 2440/20; G01N 2500/00; G01N 33/6815;
(Continued)

(56) References Cited

U.S. PATENT DOCUMENTS

| 5,951,981 A | 9/1999 | Markland, Jr. et al. |
| 11,953,436 B2 | 4/2024 | McElroy et al. |

(Continued)

FOREIGN PATENT DOCUMENTS

| CN | 105738612 A | 7/2016 |
| JP | 2010048568 A | 3/2010 |

(Continued)

OTHER PUBLICATIONS

Garrido-Medina, Raúl, et al. "Analysis of alpha-1-acid glycoprotein isoforms using CE-LIF with fluorescent thiol derivatization." Electrophoresis 33.7 (2012): 1113-1119. (Year: 2012).*

(Continued)

*Primary Examiner* — Jennifer Wecker
*Assistant Examiner* — Oyeleye Alexander Alabi
(74) *Attorney, Agent, or Firm* — Casimir Jones, S.C.; Anne M. Reynolds

(57) ABSTRACT

Embodiments described herein relate to devices, and methods for quantifying thiol content in a sample containing a mixture of proteins or protein isoforms. The method includes conjugating a portion of the sample with free thiol detection binders, separating the contents in the portion of the sample into separated protein isoforms, detecting fluorescence signals associated with each separated protein isoform, and quantifying, based on the fluorescence signals, a relative amount of free thiol associated with each separated protein isoform. In some instances, the method includes quantifying the amount of each separated protein isoform based on absorbance signals associated with each separated protein isoform. In some instances, the fluorescence and/or absorbance signals associated with protein isoforms conjugated with detection binders can be compared with the corresponding signals associated with unconjugated protein isoforms. In some instances, the method further includes
(Continued)

applying a reducing agent and quantifying total-thiol content in the sample.

21 Claims, 5 Drawing Sheets

Related U.S. Application Data continuation of application No. PCT/US2019/047965, filed on Aug. 23, 2019.

(60) Provisional application No. 62/722,012, filed on Aug. 23, 2018.

(51) Int. Cl.
*B01L 3/00* (2006.01)
*C07C 309/65* (2006.01)
*C07C 309/73* (2006.01)
*G01N 1/40* (2006.01)
*G01N 21/01* (2006.01)
*G01N 21/31* (2006.01)
*G01N 21/33* (2006.01)
*G01N 21/64* (2006.01)
*G01N 27/414* (2006.01)
*G01N 33/52* (2006.01)
*G01N 33/532* (2006.01)
*G01N 33/543* (2006.01)
*G01N 33/569* (2006.01)
*G01N 33/58* (2006.01)
*G01N 33/72* (2006.01)
*G01N 35/04* (2006.01)

(58) Field of Classification Search
CPC .... G01N 21/33; G01N 33/68; G01N 33/6854; G01N 2021/6439
See application file for complete search history.

(56) References Cited

U.S. PATENT DOCUMENTS

| 2008/0241820 A1 | 10/2008 | Krutzik et al. |
| 2010/0025245 A1 | 2/2010 | Cole et al. |
| 2012/0228519 A1 | 9/2012 | Gilmore et al. |
| 2017/0307624 A1 | 10/2017 | Kim et al. |
| 2021/0199583 A1 | 7/2021 | McElroy et al. |

FOREIGN PATENT DOCUMENTS

| JP | 2010051289 A | 3/2010 |
| WO | WO-9413829 A1 | 6/1994 |
| WO | WO-2018102759 A1 | 6/2018 |
| WO | WO-2020041740 A1 | 2/2020 |

OTHER PUBLICATIONS

Borges, C. R. et al., "Techniques for the analysis of Cysteine Sulfhydryls and Oxidative Protein Folding," Antioxidants & Redox Signaling, Jul. 2014, vol. 21, No. 3, pp. 511-531.

Extended European Search Report for European Application No. 19851480.4, mailed Apr. 5, 2022, 5 pages.

Garrido-Medina, R. et al., "Analysis of alpha-1-acid glycoprotein isoforms using CE-LIF with fluorescent thiol derivatization," Electrophoresis, Apr. 2012, vol. 33, No. 7, pp. 1113-1119.

Hansen, R. E. et al., "Quantifying the global cellular thiol-disulfide status," Proceedings of the National Academy of Sciences of the USA, Jan. 2009, Jan. 13, 2009, vol. 106, No. 2, pp. 422-427.

International Search Report and Written Opinion for International Application No. PCT/US2019/047965, mailed Nov. 13, 2019, 11 pages.

Lelova et al., "Optimization and Validation of a New Capillary Electrophoresis Method with Conductivity Detection for Determination of Small Anions in Red Wines," Food Analytical Methods, May 2018, vol. 11, pp. 1-10.

Maeda, K. et al., "Cy5 maleimide labelling for sensitive detection of free thiols in native protein extracts: identification of seed proteins targeted by barley thioredoxin h isoforms," The Biochemical Journal, Mar. 2004, vol. 378, Pt. 2, pp. 497-507.

Smolka, M. et al., "Quantitative Protein Profiling Using Two-Dimensional Gel Electrophoresis, Isotope-Coded Affinity Tag Labeling, and Mass Spectrometry," Molecular & Cellular Proteomics, Jan. 2002, vol. 1, No. 1, pp. 19-29.

* cited by examiner

SYSTEMS AND METHODS FOR THE DETECTION AND ANALYSIS OF FREE THIOL

CROSS-REFERENCE TO RELATED APPLICATIONS

This application is a continuation of U.S. patent application Ser. No. 17/181,610, filed Feb. 22, 2021, now U.S. Pat. No. 11,953,436, issued on Apr. 9, 2024, which is a continuation of International Patent Application No. PCT/US2019/047965, filed Aug. 23, 2019, which claims priority to and the benefit of U.S. Provisional Application No. 62/722,012, filed Aug. 23, 2018, entitled "Systems and Methods for the Detection and Analysis of Free Thiol," the disclosure of each of which is incorporated herein by reference in its entirety.

FIELD

Some embodiments described herein relate to systems, apparatuses and methods for the detection and analysis of free thiol in samples of biological materials.

BACKGROUND

A thiol is an organosulfur compound that includes a carbon bonded sulfhydryl (R-SH) group, R being an alkyl or aromatic or similar substituent. Thiols, also referred to as free-thiols and/or free thiol group(s), are the sulfur analogs of alcohols with sulfur taking the place of the oxygen in the hydroxyl group (—OH) of the alcohol. Thiols can also be generated by the reduction of compounds including one or more disulfide bridges or disulfide groups, which become free thiols after the reduction and contribute to the total thiol content of the compound.

Thiols play a significant role in several naturally occurring and synthetic bio-organic molecules. Free thiols in biological systems have important regulatory roles. For example, oxidatively modified thiol groups of cysteine residues are known to modulate the activity of a growing number of proteins. As another example, disulfide bond formation is a key posttranslational modification, with implications for structure, function and stability of numerous proteins. While disulfide bond formation is a necessary and essential process for many proteins, it is deleterious and disruptive for others. Cells regulate thiol-disulfide bond homeostasis, through Thiol-disulfide exchange reactions, that play critical roles in many aspects of cellular function. The detection and measurement of free thiols (e.g., thiols associated with free cysteine, glutathione, and cysteine residues on proteins) is an important tool for investigating biological processes and events in many biological systems.

Thiol groups can be present on various proteins, for example as part of cysteine residues included in the various proteins. Thiol groups can also be present on various protein isoforms, a set of highly similar proteins that perform the same or similar biological roles. A set of protein isoforms may be formed from alternative splicings or other post-transcriptional modifications of a single gene. Thiol groups may be present on synthetically derived products such as Antibody-drug conjugates (ADCs), bioconjugates, and immunoconjugates and other biopharmaceutical drugs designed as a targeted therapy for treatment of various conditions (e.g., treatment of various cancers). ADS, for example, combine the specificity, favorable pharmacokinetics, and biodistributions of antibodies with the destructive potential of highly potent drugs. For example, in some instances, ADCs can be designed to combine the targeting capabilities of monoclonal antibodies with the cancer-killing ability of cytotoxic drugs designed to discriminate between healthy and diseased tissue. Thus, unlike chemotherapy, ADCs can target and kill tumor cells while sparing healthy cells. ADCs are formed by linking or conjugating specific antibodies to specific therapeutic drugs. Thiol groups present on the antibodies can be used as linkage sites to conjugate the drug to form ADCs. In some instances, ADCs can include an antibody linked via thiol groups to a biologically active cytotoxic (anticancer) payload or drug.

Thiols are typically detected directly by virtue of their relatively high reactivity compared to most other common species in biological systems. However, significant challenges exist to analyzing thiol content in samples such as those mentioned above. For example, currently available methods of quantification of free thiols lack further specificity such as the specific proteins or protein isoforms that may include free thiol groups (for example included in cysteine residues). In the development of biologic therapeutics knowing, for example, which isoforms have particular characteristics, such as the presence of free thiol groups, is important to determine the allowable limits for each isoform.

Increasingly, alternative formats of traditional therapeutic antibodies are being developed including the use of IgG2 antibodies with additional disulfide bonds. For example, such antibodies can be used in the development of ADC (Antibody Drug Conjugates), bispecific antibodies, multi-specific antibodies, and other multivalent and/or conjugate products. Furthermore, some products may involve the reduction of antibody halves before reassembly of the final product. Additionally, the antibody for ADC products typically have engineered cysteines for attachment of the drug conjugate linker. These processes can lead to increased free thiol heterogeneity. As a result, it can be beneficial to analyze such isoforms. Known techniques for detecting free thiol content, however, are generally inadequate to detect free thiol content of such antibodies. For example, known techniques for quantifying thiol content involve testing portions of the sample with one marker at a time, which involves significant time and expense. As another example, some known methods of measuring thiol content are unable to distinguish between free thiols and disulfide bridges.

Methods to objectively identify and quantify free thiol and total thiol content in a biological sample, with specificity to individual portions of the sample such as protein isoforms are currently lacking. A need therefore exists for methods and apparatus for deconvolving protein-containing samples and analyzing the deconvolved or separated samples for free thiol and/or total thiol content.

SUMMARY

Some embodiments described herein relate to systems, apparatuses and methods for differential analysis of a sample containing of biological materials, such as protein isoforms that include thiol groups and/or disulfide bridges.

In some embodiments, a method includes generating, from a sample containing a plurality of protein isoforms at least some of which have one or more free thiol groups, a first sample portion and a second sample portion. The method includes applying, to the first sample portion, a fluorescent detection binder configured to bind to free thiol groups to produce conjugated thiols, without reducing the plurality of protein isoforms included in the first sample portion. The method includes separating the plurality of protein isoforms in the first sample portion to generate a first set of separated protein isoforms, and separating the plurality of protein isoforms in the second sample portion to generate a second set of separated protein isoforms. The method includes detecting a first fluorescence signal associated with the conjugated thiols and an absorbance signal associated with the first set of separated protein isoforms. The method further includes identifying, based on the absorbance signal, at least one of a quantity or an identity of each separated protein isoform from the first set of separated protein isoforms. The method also includes detecting a second fluorescence signal associated with the second set of separated protein isoforms, and measuring, based on a difference between the first fluorescence signal and the second fluorescence signal, a quantity of free thiol groups associated with each separated protein isoform from the first set of separated protein isoforms.

In some embodiments, a system includes a memory and a processor operatively coupled to the memory. The processor is configured to receive a fluorescence signal associated with a first set of separated protein isoforms. The first set of separated protein isoforms can be obtained from a first portion of a sample containing a plurality of protein isoforms, at least some protein isoforms from the plurality of protein isoforms having one or more free thiol groups. The fluorescence signal can be associated with a fluorescent detection binder applied to the first sample portion that is configured to bind to free thiol groups. The processor can be configured to receive a first absorbance signal associated with the first set of separated protein isoforms, and receive a second absorbance signal associated with a second portion of the sample. The processor can be further configured to identify, based on the first absorbance signal and the second absorbance signal, at least a subset of the protein isoforms from the sample, and calculate, based on the fluorescence signal, a quantity of free thiol groups associated with each protein isoform from the subset of the protein isoforms.

In some embodiments, a method includes applying, to a sample containing a plurality of protein isoforms, a set of fluorescent detection binders. The set of fluorescent detection binders can be configured to bind to free thiols without reducing protein isoforms. The method includes separating the sample via isoelectric focusing to generate a set of separated protein isoforms. The method further includes obtaining a fluorescence signal and an absorbance signal associated with the set of separated protein isoforms, identifying, based on the absorbance signal, at least one of a quantity or an identity of each separated protein isoform from the set of separated protein isoforms; and measuring, based on the fluorescence signal, a quantity of free thiols associated with each separated protein isoform from the set of separated protein isoforms.

In some embodiments, a method includes processing at least a portion of a sample containing a mixture of proteins and/or protein isoforms. The method includes preparing a sample potentially containing thiols and dividing the sample into a first and second portion. The method includes conjugating the first portion of the sample with one or more specific detection binders targeting free thiol groups to produce conjugated thiols. The method includes separating the proteins or protein isoforms in the first and second portions of the sample and performing fluorescence emission measurements on the separated contents of the first and second portions of the sample. The method further includes comparing the fluorescence measurements of the first portion of the sample, including separated proteins or protein isoforms conjugated with detection binders, against fluorescence measurements of the second portion of the sample, including separated proteins or protein isoform similar to that of the first portion but unconjugated with detection binders. The method further includes quantifying the amount of free thiol content in the separated contents of the sample based on the comparison of fluorescence measurements obtained from the separated contents of the first and second portions of the sample, described above.

In some instances, in addition to the fluorescence measurements, the method optionally includes performing absorbance measurements (e.g., ultraviolet (UV) absorbance measurements) from the separated contents of the first and second portions of the sample, and comparing the absorbance measurements of the separated contents of the first and second portions of the sample. In such instances, based on the comparison of the absorbance measurements, the method includes quantifying the amount of the separated protein or protein isoform by deconvolving and contribution of the conjugated detection binder to the absorbance (e.g., increased UV absorbance from the conjugated fluorescent dye or antibody acting as the detection binder).

In some instances, the method further includes evaluating whether the total thiol content of the sample is in the form of free thiol. For example, if the sample may include thiol and disulfide groups, the method includes determining whether there may be disulfide bridges in the sample. If the sample is determined to potentially contain disulfide groups, the method includes converting any potential disulfide groups into thiol groups using suitable methods, and conducting free thiol detection following the procedure described above, and in further detail herein.

DETAILED DESCRIPTION

Systems, methods and apparatuses of the disclosure relate to the quantification and differential analysis of free thiol content in a sample containing a mixture of proteins and/or protein isoforms.

Figure 1:
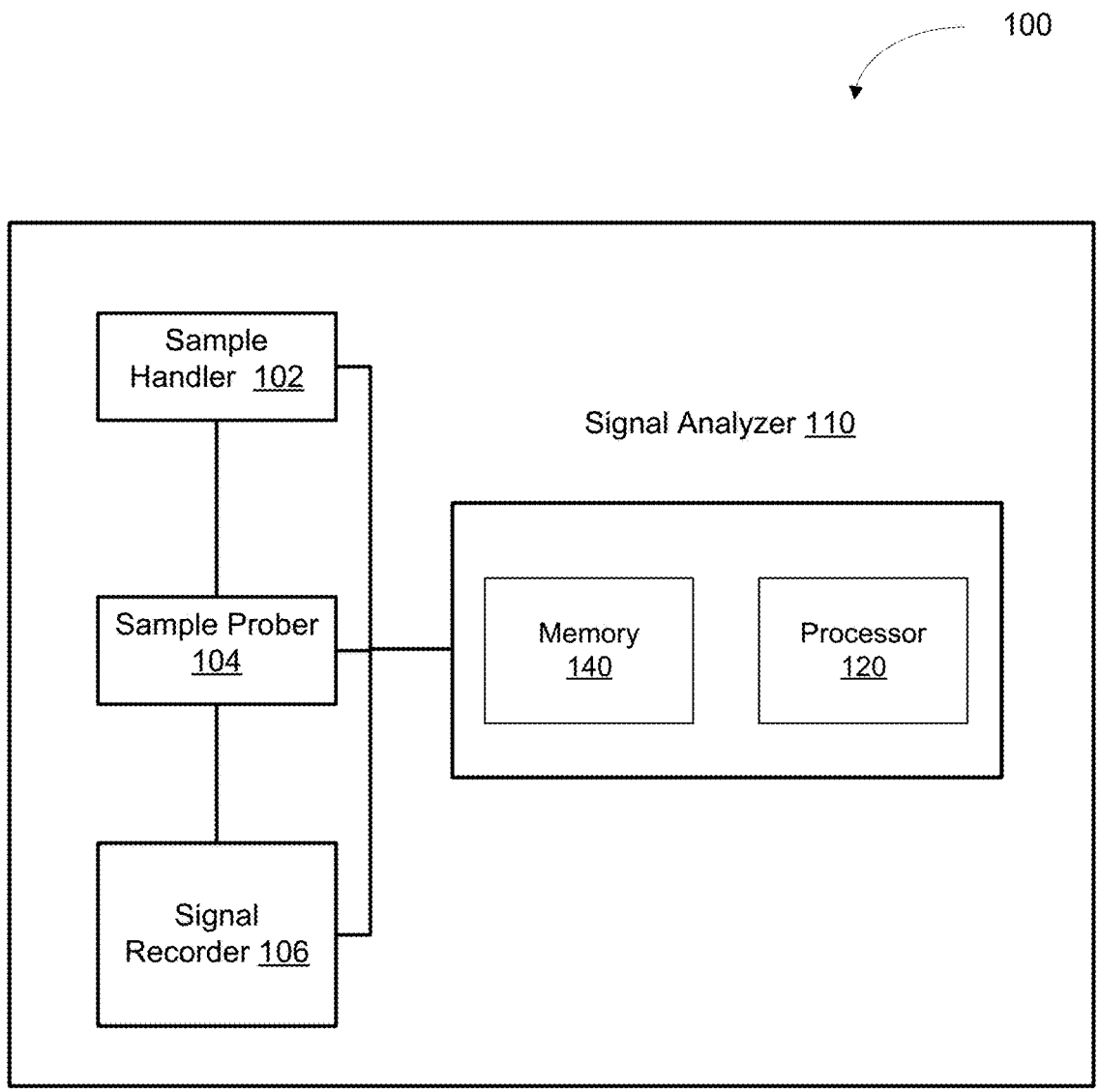
FIG. 1 is a schematic diagram of a system configured to perform differential analysis for quantifying free thiol content in a sample containing mixtures of proteins and/or protein isoforms, according to an embodiment.

FIG. 1 shows a schematic of an example Free Thiol Analysis (FTA) system 100. The FTA system (also referred to here as "the analysis system" or simply "the system") is operable to perform a differential analysis of a sample containing a mixture of proteins and/or protein isoforms to quantify the free thiol content. Performing differential analysis can include (i) separation of the contents of the sample, such as proteins and/or protein isoforms, using any suitable separation method, and (ii) using a combination of one or more types of detection binders that specifically bind to free thiol groups present on the proteins or protein isoforms in the sample to produce conjugated thiols.

The system 100 includes a sample handler 102, a sample prober 104, a signal recorder 106, and a signal analyzer 110 (also referred to as the differential analyzer or simply the analyzer). The signal analyzer 110 can be any suitable computing entity having a processor 120 and a memory 140. For example, the signal analyzer can be a personal computer, a laptop computer, an enterprise system at least partially hosted in an enterprise server, such as, for example a web server, an application server, a proxy server, a telnet server, a file transfer protocol (FTP) server, a mail server, a list server, a collaboration server and/or any other suitable computing entity.

The various components of the system 100 can be interconnected in any suitable manner (physically, fluidically, and/or electrically, e.g., through wired or wireless connection methods). In some embodiments, the signal analyzer 110 can be physically collocated with the sample handler 102, sample prober 104 and/or signal recorder 106 (e.g., disposed in the same room or within a common housing). Although not shown in FIG. 1, the system 100 can be configured to be coupled to one or more other external computing entities (e.g., personal computers, servers, cloud servers, etc., which may include a processor and a memory) in any suitable manner though a communication network or a communication channel. For example, the signal analyzer 110 can be partially and/or completely implemented using an external computing entity.

Figure 2:
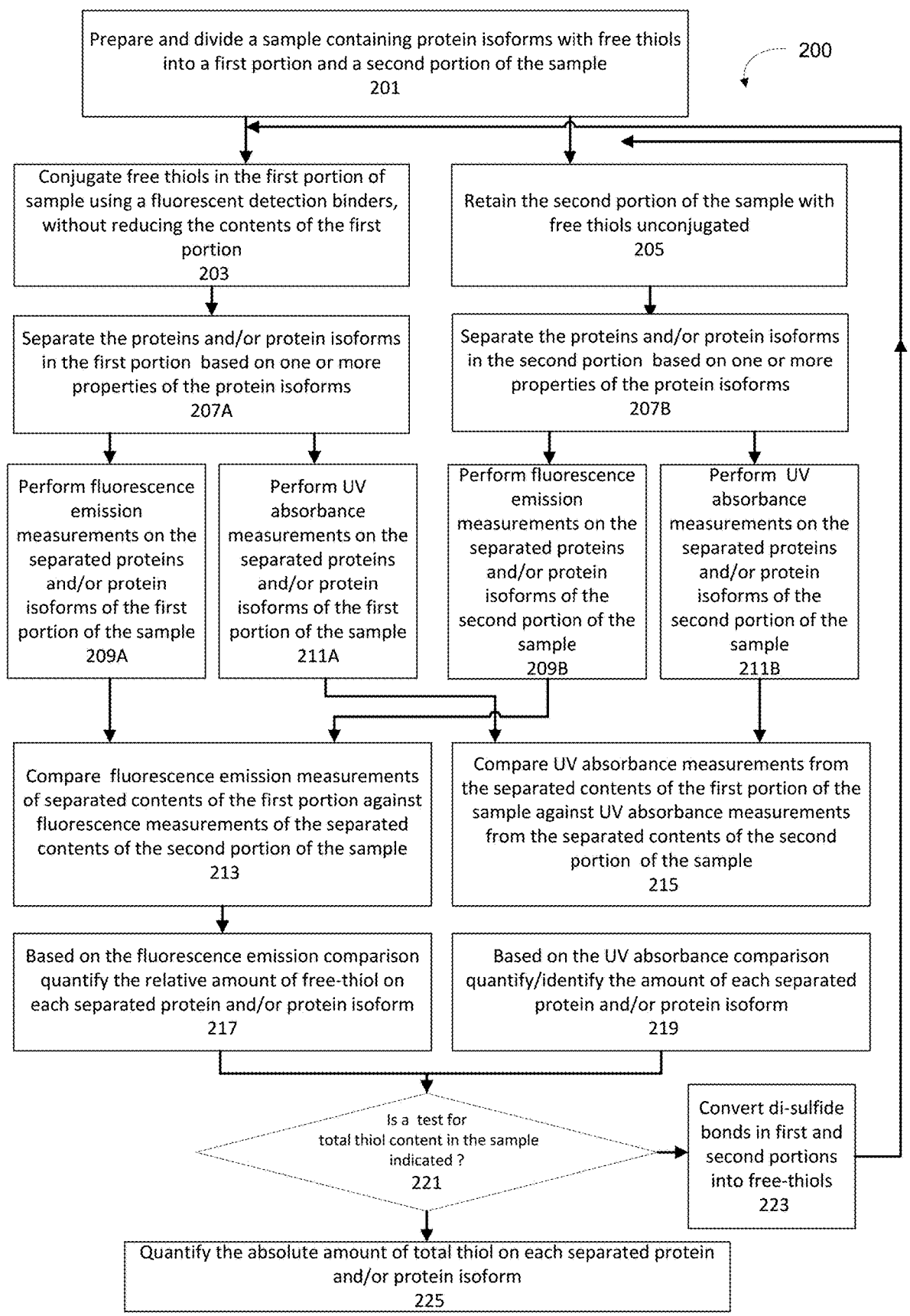
FIG. 2 is a flowchart of a method to perform a differential analysis for quantifying free thiol content in a sample containing a mixture of proteins and/or protein isoforms, according to an embodiment.

FIG. 2 is a flow chart of a method 200 of performing differential analysis to quantify free thiol and/or total thiol in a sample containing a mixture of proteins and/or protein isoforms, according to an embodiment. The method 200 can be carried out using a system described herein (e.g., system 100 described with reference to FIG. 1). In particular constituent proteins or protein isoforms can be separated and analyzed individually for their thiol content, allowing simultaneous identification of protein/protein isoforms and the quantification of free thiol content in a protein specific or isoform specific manner.

At 201, a sample containing a mixture or a plurality of proteins and/or protein isoforms is prepared. The sample can be prepared from a naturally occurring source such as a bodily fluid like plasma, blood, urine, and so forth and/or a tissue-derived sample. The sample may, in some instances, be prepared from a synthetically generated or engineered source such as a synthetic and/or recombinant antibody preparation, an Antibody-Drug-Conjugate (ADC), or the like. Preparing the sample can include (ultra)centrifugation of the sample, size exclusion chromatography, (ultra)filtration, or any other suitable means of obtaining a protein fraction or fraction containing protein isoforms from the source. In some instances sample preparation can include steps such as cell disruption, extraction, solubilization, removal of interfering compounds, changes of the physio/chemical properties and concentration of the sample, etc. In some instances, a sequence of one or more steps can be followed to prepare the sample based on properties of the sample such as type of fluid, source of fluid, medical history of the patient providing the sample, amount or quantity of the sample, etc. The prepared sample is then divided into a first portion and a second portion.

As described in further detail herein, a differential analysis of a sample containing a mixture of proteins and/or protein isoforms for quantification of free thiol content can be performed using detection binders configured to bind or form complexes with free thiol groups in the proteins or protein isoforms to produce conjugated thiols. At 203 the contents of the first portion of the sample from 201 can be conjugated with detection binders specific for thiol groups to produce conjugated thiols. A mixture containing detection binders can be combined with the first portion of the sample; the mixture can be formulated such that it results in no or minimal reducing effects on the contents of the first portion of sample.

Detection binders can be, for example, fluorescent dyes configured to selectively bind to thiol groups. For example, fluorescent modification of proteins using covalent methods can include derivatization of the proteins or proteomic samples with a fluorescent dye prior to any separation of the protein contents of the first portion of the sample, as disclosed below. Alternatively, using noncovalent methods, the proteins or isoforms in the first portion of the sample may first be separated by a suitable separation method (e.g., by capillary electrophoresis, SDS-PAGE, etc.) and then the separated protein or isoform bands may be stained with dyes that bind to SDS-protein complexes, e.g., the SYPRO dyes. The dyes can be configured to be non-reducing such that the dyes specifically target free thiol groups in the sample without altering existing disulfide bonds in the sample.

An example of covalently labelling thiol groups of proteins and protein isoform mixtures with fluorescent dyes at 203 is to label the cysteine (Cys) residues of the proteins and protein isoforms with thiol-reactive dyes, such as iodoacetamide dyes (e.g., BODIPY TMR cadaverine IA and BODIPY FI CI-IA, -TMRIA and eosin-5-iodoacetamide), or maleimide dyes (e.g., ThioGlo I and Rhodamine Red C2 maleimide). Dyes may be selected based on properties such as desired dye concentration, the amount of thiol content expected, the concentration of the protein and/or protein isoform content in the first portion of the sample, the specificity of binding to thiol groups under the desired dye concentration, etc.

At 205, the second portion of the sample is retained. The second portion of the sample remains unconjugated to any detection binder and is retained for use as a reference sample to analyze the contents of the first portion as discussed in further detail herein.

At 207A, the contents of the first portion of the sample, conjugated with detection binders (e.g., fluorescent dyes) at 203, are separated using any suitable separation method to generate a set of separated protein isoforms. In some embodiments, a sample handler (e.g., sample handler 102) can be used to separate the first portion of the sample to generate the separated protein isoforms. For example, proteins with varying charge, size, mobility, and/or molecular weight may be separated using methods like electrophoresis such as imaged capillary electrophoresis, SDS-PAGE, or other suitable technique. As another example, proteins and/or protein isoforms (conjugated to detection binders) may be separated based on their isoelectric point with methods like (capillary or gel-based) Isoelectric Focusing (IEF). After separation, the contents of the first portion of the sample may be in the form of separated bands of proteins and/or protein isoforms, optionally immobilized in a medium such as a gel or capillary. In some instances, as disclosed above, the proteins and/or protein isoforms can first be separated (e.g., as described at 207A of flowchart 200) and the separated bands of proteins and/or protein isoforms can be conjugated with non-covalent dyes (e.g., as described at 203 of flowchart 200).

At 207B, the contents of the second portion of the sample (the portion that is unconjugated with detection binders) is made to undergo a similar separation procedure as the first portion of the sample at 207A After separation, the contents of the second portion of the sample may be in the form of separated bands of proteins and/or protein isoforms, optionally immobilized in a medium such as a gel or capillary. For example, a sample handler (e.g., sample handler 102) can separate the second portion of the sample into separated protein isoforms. In some implementations, sample handling and/or separation can be done in a plate format. In some embodiments, the separation of the contents of the first portion of the sample and the contents of the second portion of the sample can be performed simultaneously and/or in parallel. For example, the first portion of the sample and the second portion of the sample can be separated in parallel capillaries or gel-lanes defined in a sample handler (e.g., sample handler 102 described herein) during a single separation run. In other embodiments, the contents of the first portion of the sample and the second portion of the sample can be separated in different/sequential separation runs.

At 209A, the bands of separated proteins and/or protein isoforms of the first portion of the sample, conjugated to detection binders, are detected via a fluorescence emission measurement. In some embodiments, a sample prober (e.g., sample prober 104) can be used to induce and/or measure fluorescence emission from the conjugated detection binders. For example, light of a suitable wavelength (e.g., selected to match the excitation spectrum of the detection binders used) and suitable intensity may be used to probe the medium containing the separated bands of conjugated proteins or protein isoforms, for a predetermined period of time (also referred to herein as "exposure") and excite the conjugated fluorescent dyes, using suitable fluorescent imaging techniques. Fluorescence signals may be emitted in response to the excitation light probe. Because the detection binders selectively bind to thiol groups, the fluorescence signals can be associated with the conjugated thiols. The emitted fluorescence signals, which can be correlated to thiol-groups in the separated bands of conjugated proteins and isoforms, are detected, recorded and/or stored for further analysis. In some embodiments, the emitted fluorescence signals can be detected and/or quantified using a signal recorder (e.g., signal recorder 106) to obtain fluorescence measurements. In some instances, the detected fluorescence signals can be analyzed and transformed into a suitable representation, for example representations in the form of graphs of signal intensity as a function of time of recording or as graphs of signal intensity as a function of position of scanning. In some instances, the recorded fluorescence signals may be transformed into a form of a spatial map of the medium in two or three spatial dimensions, with or without a temporal dimension corresponding to time of recording of the signals. In other words, the representation of the medium can in some instances be an image or a three-dimensional stack of images, each image corresponding to a single instance capture of a two- or three-dimensional view of the medium with pixels corresponding to positions along predetermined axes on the medium. The representation of the medium can in other instances be a video of a two- or three-dimensional spatial region captured over a time period. The representation of the medium can be include the separated bands of conjugated proteins and/or protein isoforms, with fluorescence intensity varying as a function of thiol content.

At 209B, the bands of separated proteins or protein isoforms of the second portion of the sample, unconjugated to detection binders, are probed using similar techniques as those discussed above with reference performing fluorescence emission measurements at 209A. In some instances, a native fluorescence (or auto-fluorescence) signal can be captured from the separated proteins or protein isoforms of the second portion of the sample, unconjugated to detection binders. In some embodiments, a sample prober (e.g., sample prober 104) can be used to induce and/or measure native fluorescence emission from the conjugated detection binders. For example, light of the same wavelength or frequency and intensity used to induce fluorescence emission may be used to probe the medium containing the separated bands of unconjugated proteins or protein isoforms, using the same or similar fluorescent imaging techniques as in 209A. The signals in response to the light probe can be recorded and stored in a manner similar to that performed at 209A. In some embodiments, the emitted native fluorescence signals can be detected and/or quantified using a signal recorder (e.g., signal recorder 106) to obtain native fluorescence measurements. For example, the signals in response to the excitation light probe may be an image containing a spatial map of the medium containing the separated bands of conjugated proteins and/or protein isoforms. However, unlike the results at 209A, the map obtained at 209B may lack any significant fluorescence intensity that corresponds to an indication of thiol content. The measurement of fluorescence emission at 209A and 209B may be conducted sequentially or in a substantially parallel manner.

At 213, the fluorescence measurements recorded from the separated contents of the first portion (conjugated with fluorescent dyes) at 209A, and the fluorescence measurements obtained from the separated contents of the second portion (unconjugated) of the sample (also referred to as native fluorescence) are compared. The relative amount of free thiol content in the sample is determined at 217 based on the comparison performed at 213. For example, in some instances the relative amount of free thiol content in the sample can be determined based on a difference between the fluorescence measurements recorded from the separated contents of the first portion conjugated with florescent detection binders and the native fluorescence measured from the separated contents of the second portion unconjugated with detection binders. In some instances, as described above, the results from 209A and 209B may be in the form of images containing spatial maps of the separated proteins and/or protein isoforms, with corresponding locations of the medium at 209A and 209B (e.g., locations in a capillary, on a SDS-PAGE gel, or a IEF medium) containing the same protein or isoform in the conjugated form (209A) and in the unconjugated form (209B), respectively. Thus, the resulting fluorescence image containing spatial maps of the medium from 209A and 209B may contain fluorescence signatures indicating the presence and absence of fluorescent dyes on the same proteins or protein isoforms, respectively. In some instances, depending on the detection binders used to bind free thiol in the first portion of the sample, there may be shifts or differences in the relative locations of the separated bands of conjugated proteins or isoforms with reference to the locations of the unconjugated proteins or isoforms of the same identity. For example, the detection binders may alter the mobility, isoelectric point, or other characteristic of the proteins or isoforms. Such shifts may be taken into consideration during any analysis of results based on the separated bands of proteins or isoforms (e.g., during the analysis of fluorescence emission or UV absorbance as described below).

As described above, the image from 209A shows fluorescence signals indicating the locations where specific proteins or protein isoforms are located, with the fluorescence intensity corresponding with the amount of thiol content. Whereas, the image from 209B, taken of the second portion of the sample, which lacks thiol-specific fluorescent dyes, is expected to show reduced or minimal fluorescence signals at the locations where specific proteins or protein isoforms are expected to be immobilized (with fluorescence detected being caused by auto-fluorescence or background materials in the sample or medium that may cause some non-zero amount of fluorescence emission). Thus, fluorescence measured in the background condition from 209B can be used as a reference to quantify the amount of thiol content. The fluorescence measured in the background condition from 209B can be subtracted from (or otherwise used to correct) the intensity of fluorescence accounted for by the presence of fluorescence dyes in the results from 209A. In other embodiments, the relative amount of free thiol content in the sample can be determined based solely on the fluorescence measured at 209A.

As indicated in the flowchart 200, in some instances the method includes measurement of an absorbance signal (e.g., signal associated with UV absorbance). At 211A, the separated contents of the first portion of the sample, conjugated with fluorescent dyes, is probed with suitable stimulus such as UV light, and the resulting absorbance signal (also referred to herein as "absorbance") is measured. In some embodiments, a sample prober (e.g., sample prober 104) can be used to probe the separated protein isoforms of the first portion of the sample with UV light and a signal recorder (e.g., signal recorded 106) can be used to measure relative absorption of UV light associated with each separated protein isoform of the first portion of the sample. Similarly, at 211B, the same light or a similar stimulus at a similar intensity is used and the amount of absorbance by the separated contents of the second portion of the sample can be recorded. In some embodiments, a sample prober (e.g., sample prober 104) can be used to probe the separated protein isoforms of the second portion of the sample with UV light and a signal recorder (e.g., signal recorded 106) can be used to measure relative absorption of UV light associated with each separated protein isoform of the second portion of the sample. In some implementations, the separated protein isoforms from the first portion and the second portion can be probed simultaneously and the relative UV absorbance associated with each separated protein isoform of both portions can be recorded simultaneously.

As described with reference to results from 209A and 209B, the results from 211A and 211B can be in the form of images containing spatial maps of UV absorbance corresponding to different separated proteins and/or protein isoforms. The measurement of absorbance at 211A and 211B may be conducted sequentially or in a substantially parallel manner.

In some implementations, the fluorescence measurements described at 209A and 209B, and the UB absorbance measurements described at 211A and 211B can be performed simultaneously using one or more sample probers (e.g., sample prober 104) and one or more signal recorders (e.g., signal recorder 106). For example, a system may be configured such that a single sample prober (e.g., UV light source) can induce both fluorescence emission as well as UB absorbance. As another example, a signal recorder can include one or more detection arms configured to detect and/or record fluorescence signals and UV absorbance signals from the separated protein isoforms from the first and/or second portions of the sample, simultaneously.

The absorbance signal can be used to identify a quantity and/or an identity of each separated protein and/or protein isoform from the set of separated proteins/protein isoforms. At 215, the absorbance measurements of the separated contents of the first portion is compared against the absorbance of the separated contents of the second portion. At 219, based on the comparison at 215, the amount and/or identity of a specific protein and/or protein isoform. For example, an increased UV absorbance may be observed at 211A, and the increased absorbance may correspond to the conjugated dye. Thus, the increased UV absorbance associated with the conjugated fluorescent dye can be accounted for, and the amount of the particular isoform can be determined. For example, UV absorbance can be used to determine relative and/or absolute quantities and/or concentrations of protein isoforms. The position of peaks associated with absorbance signals of proteins and/or protein isoforms observed at 211A and/or 211B can be used to identify the proteins and/or protein isoforms, for example, by isoelectric point, molecular weight, etc.

In some instances, the measurements of fluorescence emission (at 209A, 209B) and the measurements of UV absorbance (211A, 211B) may be conducted in a sequential manner with the former following the later or vice versa. In some other instances, the measurements of fluorescence emission (at 209A, 209B) and the measurements of UV absorbance (211A, 211B) may be conducted in a substantially parallel manner. In some instances, the measurement of fluorescence emission (at 209A, 209B) and the measurement of UV absorbance (211A, 211B) can be conducted substantially simultaneously. For example, an absorbance light source and a fluorescence excitation light source can illuminate the sample simultaneously and/or in sequence, in real time—while the proteins and/or protein isoforms are being separated. In some implementations, the absorbance light source and the fluorescence excitation light can be a single light source emitting light in the UV range (e.g., 280 nm). In other implementations, the absorbance light source and the fluorescence excitation light can be different light sources and/or emit light at different wavelengths. Similarly, the comparison (at 213) and quantification of free thiol content (at 217) and the comparison (215) and quantification/identification of proteins and/or protein isoforms (at 219), can be conducted in a sequential manner (with the former following the latter or vice versa) or substantially parallel manner. Thus, in some embodiments, a single run containing the first portion of the sample and the second portion of the sample (e.g., in different lanes or capillaries) can be analyzed for fluorescence and absorbance.

At 221, the method includes querying if a test for the total thiol content of the sample (and/or the total thiol content of one or more separated bands) is indicated. For example, in some instances, a user may indicate a test for total thiol content of the sample to be performed. In such instances, the method 200 can be used to test and/or quantify, in addition to the thiol groups in the form of free thiol, if there remain functional groups that may be converted to thiols. For example, the method at 221 may determine that the total thiol content is of the sample is to be quantified, as the sample may include disulfide groups that may be converted to thiols. In some instances, such a determination may be made following 201 to 219 having been carried out with a given sample without reducing the sample. In some instances, the test for total thiol content may be indicated and performed without performing the steps 201 to 219, i.e., without quantifying relative free thiol content.

If a test and/or quantification of total thiol content is positively indicated at 221, at 223 disulfide groups can be converted to free thiol groups using suitable procedures. For example, treating the first and second portions of the sample with suitable reductants of suitable concentration may convert the disulfide bonds to free thiol groups. Following which the process outlined in the flowchart 200 from 203 and 205 (for each of the first and second portions of the sample) to 217 and 219 can repeated to determine a total thiol content (e.g., on a per-band/per-isoform basis). A difference in detected thiol content during a second examination of the first and second portions of the sample after reducing sample can be used to determine the absolute and/or relative quantities and/or concentration of converted thiol content (e.g., quantifying disulfide groups).

In some instances, the total thiol in a sample containing free thiol and disulfide groups that can be converted to thiol groups can be quantified as described above, by following the procedure outlined in the flowchart 200 in two runs, a first run configured to determine the free thiol content in the sample and the second run configured to determine the total thiol content, including the converted thiol groups (e.g., thiol groups formed by reducing disulfide groups). In some instances, the quantification of free thiol and total thiol content can be accomplished in a single run by having four portions of the sample examined concurrently. For example, portions A and B can be obtained from a source of proteins and/or protein isoforms without reduction of potential disulfide bonds, and portions C and D can be obtained from the same source of proteins and/or protein isoforms and subjected to a suitable reducing agent to convert disulfide groups into free thiols. Thiols in the four portions A, B, C, and D (on a per-band and/or per-isoform basis) can be quantified using the procedure outlined in the flowchart 200 in FIG. 2, with portions A and B forming a first set of first and second portions, respectively, and portions C and D forming a second set of first and second portions, respectively. In other words, the portions A and C can be treated as the first portion in flowchart 200, and the portions B and D can be treated as the second portion in flowchart 200, as described at steps 201-211. Thus, fluorescence emission measurements and/or absorbance measurements can be obtained for up to all four portions of the sample, A, B, C, and D. At 213, the fluorescence emission measurements of portion A is compared to that of B, and the fluorescence emission measurements of portion C is compared to that of D. At 217, based on the fluorescence emission measurement comparison between portions A and B, the relative amount of free thiol in the unreduced portions, A and B, is quantified. Additionally, at 217, based on the fluorescence emission measurement comparison between portions C and D, the total amount of thiol in the reduced portions, C and D, is quantified. Then, at 225, the quantified amount of free thiol from the portions A and B is compared with the quantified amount of total thiol from portions C and D and the amount of converted thiol can be determined. For example, the difference between the total thiol quantification and the free thiol quantification can be used to deduce the amount of converted thiols present in the reduced portions C and D, which may have resulted from reduction of disulfide bonds in the original source from which comparable portions A, B, C, and D were obtained. Furthermore, at 215, the absorbance measurements from the portion A can be compared to that from portion B, and the absorbance measurements from portion C can be compared to that from portion D. At 219, based on the absorbance measurement comparison between portions A and B, the relative amount of each separated protein and/or protein isoform in the unreduced portions, A and B, is identified and/or quantified. Additionally, at 219, based on the absorbance measurement comparison between portions C and D, the relative amount of each separated protein and/or protein isoform in the reduced portions, C and D, is identified and/or quantified. The identified and/or quantified proteins and/or protein isoforms from the various portions can be compared for confirmation and/or control that the reduced portions (A and B) are substantially similar to the reduced portions (C and D), accounting for effects of reduction and/or conjugation with binders. In some instances the identified and/or quantified proteins and/or protein isoforms from the various portions can be compared for quantification of the effects of reduction (e.g., reduction of disulfide bonds) or the effects of conjugation with suitable binders (e.g., antibodies).

The processes described above can also be used, in some instances, to quantify total thiol in a sample without the quantification of free thiol, by using already reduced samples as the first and second portions described in flowchart 200. Furthermore, in some instances, the fluorescence measurements can be carried out without absorbance measurements. Similarly, in some instances, absorbance measurements of the first and second portions can be carried out without the fluorescence measurements.

As described previously, the processes described above can be conducted in a system described herein such as the system 100 described above. In some instances, one or more of the steps in method 200 can be conducted for several samples in a parallel manner, for example using a multi-well plate to hold sample portions, etc. In some instances, one or more steps of the method 200 can be omitted. In some instances, the steps of the method 200 can be performed in any suitable order. In some instances, the method 200 can include other steps not shown in FIG. 2 to perform the quantification of free thiol and/or total thiol in a sample containing a mixture of proteins and/or protein isoforms, as described in the method 200.

Figure 3:
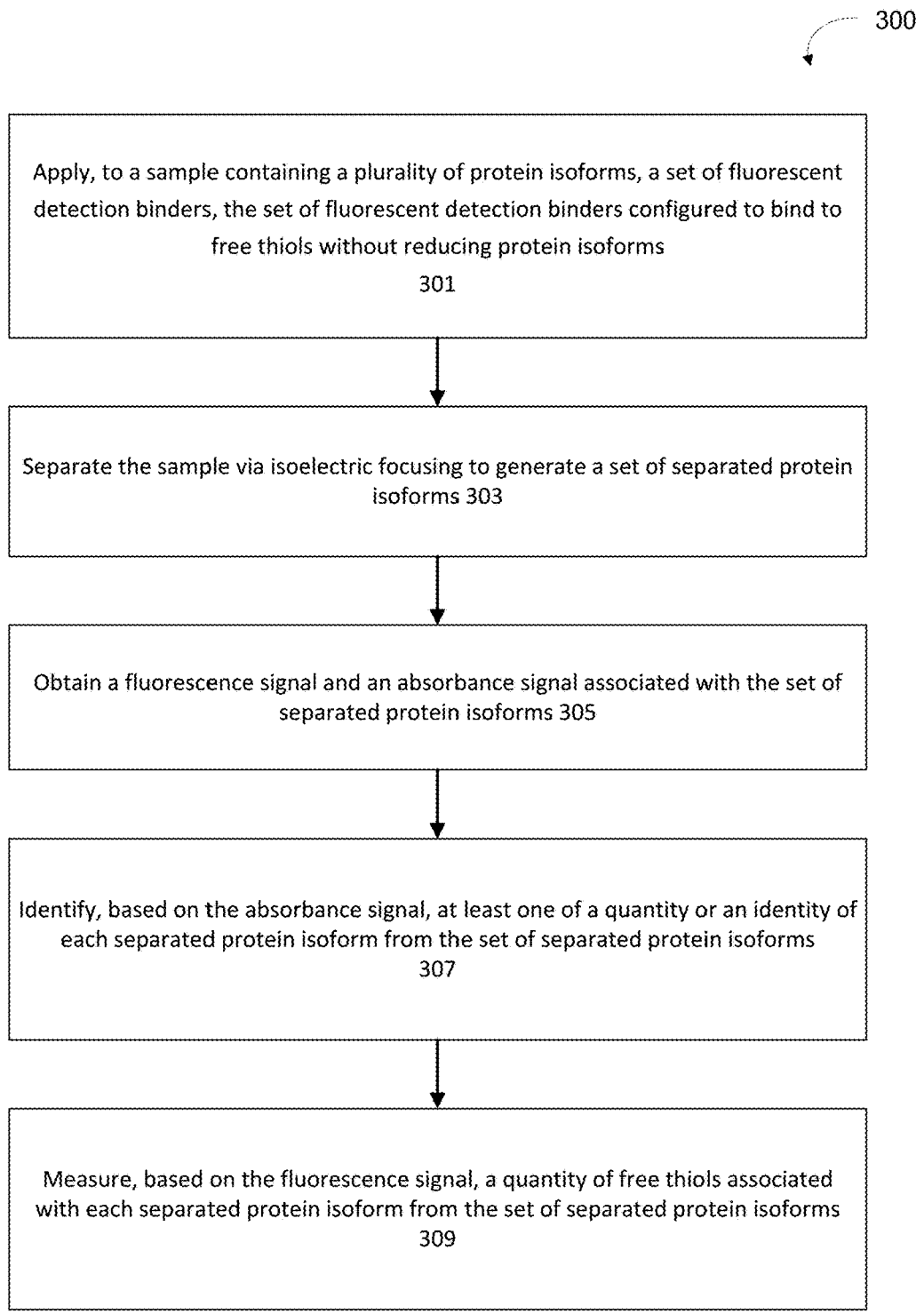
FIG. 3 is a flowchart of a method to perform a differential analysis for quantifying free thiol content in a sample containing a mixture of proteins and/or protein isoforms, according to an embodiment.

FIG. 3 is a flow chart of an example method 300 of performing differential analysis to quantify free thiol in a sample containing a plurality of proteins and/or protein isoforms, according to an embodiment. In some instances, portions of the method 300 can be substantially similar to the method 200 described above and can carried out using a system described herein (e.g., system 100 described with reference to FIG. 1). In particular, proteins or protein isoforms can be separated and analyzed for their thiol content, allowing simultaneous identification of protein/protein isoforms and the quantification of free thiol content in a protein specific or isoform specific manner.

At 301, one or more fluorescent detection binder can be applied to a sample containing a proteins and/or protein isoforms. Fluorescent detection binder(s) can be configured to bind to free thiols without reducing proteins and/or protein isoforms. As described previously with reference to the method 200, the sample can be prepared from a naturally occurring source such as a bodily fluid like plasma, blood, urine, and so forth and/or a tissue-derived sample. The sample can be prepared from a synthetically generated or engineered source such as a synthetic and/or recombinant antibody preparation, an Antibody-Drug-Conjugate (ADC), or the like, via any suitable process including cell disruption, extraction, solubilization, removal of interfering compounds, changes of the physio/chemical properties and concentration of the sample, (ultra)centrifugation, size exclusion chromatography, (ultra)filtration, or any other suitable process of obtaining a protein fraction or fraction containing protein isoforms from the source. In some instances, as described with reference to method 200, the sample can be divided into two or more portions and treated separately. The fluorescent detection binders can be substantially similar to the fluorescent detection binders described with reference to the method 200 (e.g., fluorescent detection binders described as used at 203 of method 200). For example, the fluorescent detection binders can be, fluorescent dyes configured to selectively bind, via covalent or non-covalent bonds, to free thiol (—SH) groups, be excited by light of a particular predetermined first wavelength or first band of wavelengths, and emit light at a predetermined second wavelength or second band or wavelengths. As described previously, the fluorescent detection binders can be configured to be non-reducing such that the dyes specifically target free thiol groups in the sample without altering existing disulfide bonds in the sample. In some implementations, the fluorescent detection binders can be configured to not altering a charge heterogeneity associated with a plurality of protein isoforms such that the plurality of protein isoforms can be separated using methods that take advantage of the charge heterogeneity. For example, the fluorescent detection binders can be configured to not shift the isoelectric points of a plurality of protein isoforms such that a separated protein isoform can be identified based on its isoelectric point pI. In some implementations, the fluorescent detection binders can be configured to be UV excitable such that exposure to light of a single wavelength in the UV range (e.g., 280 nm) can be used to obtain the fluorescence signal as well as the absorbance signal described below.

At 303, the method 300 includes separating the sample via isoelectric focusing (or any other suitable technique) to generate a set of separated protein isoforms. In some instances, the sample can be separated into a set of separated protein isoforms via imaged capillary isoelectric focusing (icIEF), each separated protein isoform including one or more free thiols. In some instances, the fluorescent detection binders can be configured to not modify specific properties of the plurality of protein isoforms such that each protein isoform of the plurality of protein isoforms can be identified even when conjugated with the fluorescent binder. For example, in some implementations, the fluorescent binders can be configured to bind to free thiols without altering a charge distribution associated with a plurality of protein isoforms such that the plurality of protein isoforms bound by the fluorescent detection binders can be separated and/or identified using a suitable method.

As an example, the protein isoforms can be separated to generate a set of separated protein isoforms of the plurality of protein isoforms using imaged capillary isoelectric focusing (IEF). Briefly, in some implementations, IEF can involve introducing an ampholyte solution including the sample containing a plurality of protein isoforms, bound to fluorescent detection binders, into one or more immobilized pH gradient (IPG) gels. IPGs can be acrylamide gel matrix co-polymerized with a pH gradient, which can result in stable gradient across a range of pH values. The IPG can be subjected to an applied electric field by applying a voltage (e.g., a DC voltage by applying a predetermined current) via a set of electrodes (e.g., an anode and a cathode). The immobilized pH gradient can be obtained by the continuous change in the ratio of immobilines (weak acids or bases defined by their pK value). A protein isoform, introduced in the pH gradient, that is in a pH region below its isoelectric point (pI) can be positively charged and be induced to migrate toward the cathode (negatively charged electrode). As it migrates through a gradient of increasing pH, however, the protein isoform's overall charge can decrease until the protein isoform reaches a pH region that corresponds to its pI. At this point, the protein isoform can have no net charge and so migration ceases (as there is no electrical attraction toward either the anode or the cathode). As a result, the protein isoforms can become separated protein isoforms focused into sharp stationary bands with each protein isoform positioned at a point or location in the pH gradient corresponding to its pI. Each separated protein isoform can be identified based on the isoelectric point (pI) of that protein isoform, the isoelectric point being based on the charge heterogeneity or charge distribution associated with that separated protein isoform.

At 305 the method 300 includes obtaining a fluorescence signal and an absorbance signal associated with the set of separated protein isoforms. The fluorescence signal can be associated with the fluorescent detection binders configured to bind to free thiols. Said in another way, the fluorescence signal can be associated with the conjugated thiols produced by a fluorescent detection binder binding to free thiol groups on the separated protein isoforms. As described previously, the fluorescent signal can be obtained by exciting the fluorescent detection binders bound to the separated protein isoforms with a light of suitable wavelength to induce fluorescent radiation emission of a particular band of wavelengths (e.g., 458 nm). In some implementations, the system can include one or more optical filters (e.g., a 458 nm long-pass optical filter configured to allow passage of light of wavelength greater than 458 nm while blocking wavelengths less than 458 nm or any other suitable predetermined band of wavelengths) to isolate and obtain a fluorescence signal of the band of wavelengths of interest. In some instances, the method 300 can include one or more steps (not shown in FIG. 3) of obtaining a native fluorescence signal from a portion of the sample (e.g., a portion of the sample not conjugated with any fluorescent detection binders). In some instances, the fluorescence signal associated with the fluorescent detection binders configured to bind to free thiols can be compared with the native fluorescence to determine the quantity of free thiols as described below.

The absorbance signal can be obtained by illuminating the separated protein isoforms bound by light of a suitable wavelength (e.g., UV light at 280 nm) that is known to be differentially absorbed by the separated proteins isoforms. In some implementations, the system can include one or more optical filters (e.g., a short-pass optical filter configured to allow passage of light of wavelength less than or equal to 280 nm while blocking wavelengths greater than 280 nm or any other suitable predetermined band of wavelengths) to isolate and obtain an absorbance signal of the band of wavelengths of interest (e.g. 280 nm). In some implementations, light of a single wavelength (e.g., UV light of 280 nm wavelength) can be used to obtain the UV absorbance signal as well as excite obtain the fluorescence signal At 307, the method 300 includes identifying, based on the absorbance signal, at least one of a quantity or an identity of each separated protein isoform from the set of separated protein isoforms. The absorbance signal can include a differential UV absorbance associated with each separated protein isoform from the sample, which can be used to identify each separated protein isoform. For example, a differential UV absorbance associated with a set of separated protein isoforms can be based on the amino acid composition of each separated protein isoform with the one or more amino acids included in each separated protein isoform contributing differentially to the net UV absorbance of that separated protein isoform. In some implementations, each separated protein isoform can be identified based on the differential UV absorbance associated with that separated protein isoform. In some implementations, the intensity of absorbance signal can be proportional to the amino acid composition of the separated protein isoform. In some implementations, the intensity of absorbance signal can be associated with one or more peaks each peak corresponding to a separated protein isoform. The intensity of each peak can be associated with the identity of the separated protein isoform that the peak corresponds to.

In some implementations, the fluorescent detection binders conjugated with each separated protein isoform can contribute to an absorbance signal, which can result in an increased absorbance associated with the combination of the separated protein isoform and the conjugated fluorescent detection binder. In some such implementations, a second absorbance signal can be obtained (not shown in FIG. 3) from a second set of separated protein isoforms from a second portion of the sample (e.g., a portion of the sample not conjugated with any fluorescent detection binders). The first absorbance signal from separated protein isoforms conjugated with fluorescent detection binders can be compared with the second absorbance signal without the contribution of the detection binders to determine the quantity or the identity of each separated protein isoform.

At 309, the method 300 includes measuring, based on the fluorescence signal, a quantity of free thiols associated with each separated protein isoform from the set of separated protein isoforms. In some implementations, the intensity of fluorescent radiation emitted can be proportional to the number of fluorescent binders, which can be based on the number of free thiols associated with each separated protein isoform. In some instances, a difference between the fluorescence signal associated with the fluorescent detection binders bound to free thiols and a native fluorescence obtained from a portion of the sample not conjugated with any fluorescent detection binders can be used to determine the quantity of free thiols. In some implementations, the intensity of fluorescence signal can be associated with one or more peaks each peak corresponding to a separated protein isoform. The intensity of each peak can be associated with the relative free thiol content of the separated protein isoform that the peak corresponds to.

In some implementations, the system can correlate between the measured quantity of free thiols and the resolved identity of each separated protein isoform to return a measure of free thiol associated with each identified protein isoform included in the plurality of protein isoforms contained in the sample. In some implementations, the absorbance signal and the fluorescence signal can be obtained-simultaneously or substantially simultaneously (e.g., within 10 seconds of each other). For example, the system can include an excitation sources (e.g., light source) and an absorbance source (e.g., UV light) that can be operated simultaneously to induce fluorescence radiation emission and absorption (e.g. UV absorption) such that the emitted fluorescence signal and the absorbance signal can be obtained simultaneously and/or substantially simultaneously (e.g., by the same or independent optical sensors, optionally equipped with suitable optical filter combinations).

In some implementations, the system described herein can measure the quantity of each separated protein isoform from the set of separated protein isoforms. Based on the quantity of each protein isoforms and the corresponding quantity of free thiol groups associated with that protein isoform the system can determine, for each separated protein isoform, a number of free thiol groups associated with that protein isoform.

As described previously, in some implementations, the systems and methods described herein can be used to determine a total thiol content of a set of protein isoforms. The proteins and/or protein isoforms of a sample can be reduced to generate free thiol groups from disulfide groups and the determination of a quantity of free thiol groups can be carried out as described above. For example, the quantity of a first set of free thiol groups can be determined without reducing the protein isoforms in the sample by using a first portion of the sample, as described above. Following which, another second portion of the sample can be used to determine the total thiol content. The total thiol content can be determined by applying, to the second portion of the sample, a reducing agent configured to reduce disulfide groups to generate a second set of free thiol groups additional to the first set of free thiol groups.

The quantity of total thiol content can be determined by following the procedure described above with reference to determining the quantity of free thiol groups. For example, the quantity of total thiol can be determined by applying fluorescent detection binders to the reduced second portion of the sample, separating the plurality of protein isoforms in the second sample portion to generate a second set of separated protein isoforms, detecting a fluorescence signal associated with the second set of conjugated thiols and a second absorbance signal associated with the second set of separated protein isoforms. The quantity and or identity of each separated protein isoform from the second set of separated protein isoforms and the associated total thiol content can be determined based on the second absorbance and second fluorescence signals. As described previously, in some implementations, an unconjugated portion of the reduced portion of the sample can be used to obtain a native fluorescence signal and/or an absorbance signal devoid of contribution from the fluorescent binders. A difference between a total fluorescence signal, obtained from each separated protein isoform from the second sample portion, and the native fluorescence signal, from each separated protein isoform from the second sample portion, can be used to calculate an intensity of fluorescence signal associated with conjugated free thiols produced from binding fluorescent detection binders to the total thiol content. The absorbance signal devoid of contribution from the fluorescent binders can be used to identify the separated protein isoforms in the second portion of the sample.

In some implementations, as described in further detail below (e.g., with reference to FIG. 5) the examination of a sample containing protein isoforms with free thiol groups, using systems and methods described herein, can include an examination of the detection binders (e.g., fluorescent dyes) in a state that is unbound or unconjugated with any protein isoforms, also referred to as "dye blank". In addition to detection and measurement of signals (e.g., fluorescence and absorbance signals) associated with detection binders conjugated with protein isoforms, a system can acquire signals (e.g., fluorescence and absorbance signals) from the dye blank or the detection binders (e.g., fluorescent dyes) that are unbound or unconjugated with any protein isoforms to be used as reference signals. (e.g., reference signals 471 and 481 in FIG. 5). The reference signals can be used to ascertain that no spurious peaks due to artifacts (e.g., not associated with any protein isoforms) are detected and/or misidentified. In some instances, the reference signals can also be used to quantify accurate fluorescence and/or absorbance signals using accurate baseline values. For example, a difference between the fluorescence signal acquired from detection binders conjugated to free thiols on protein isoforms and the fluorescence signal acquired from detection binders unbound to any protein isoforms can be used as an accurate florescence signal. A difference between the absorbance signal acquired from detection binders conjugated to free thiols on protein isoforms and the absorbance signal acquired from detection binders unbound to any protein isoforms can be used as an accurate absorbance signal.

In some instances, the systems and methods described herein can be used to compute a difference between the quantity of total thiol and the quantity of the first set of free thiol groups, to determine the quantity of second set of thiol groups generated from reducing disulfide groups in the second portion of the sample Based on the quantity of second set of thiol groups and a quantity of each protein isoform the system can calculate a quantity of disulfide groups included in each protein isoform of the plurality of protein isoforms included in the sample.

The systems and methods described herein can be used to determine an absolute quantity of free thiol in a protein isoform. For example, in some instances, the systems and methods described herein can include applying the fluorescent detection binder to a standard sample that includes a known quantity of free thiol groups to obtain a standardized fluorescent signal. The fluorescent signal obtained from a separated protein isoform including thiol groups (e.g., free thiol groups from a non-reduced sample or a reduced sample) conjugated with the fluorescent detection binders can be compared to the standardized fluorescent signal and, based on the comparison, an absolute quantity of thiol groups in the separated protein isoform can be computed. For example, the absolute quantity of thiol groups (free thiol groups and/or total thiol groups) in the separated protein isoform can be computed from a ratio of the fluorescent signal obtained from a separated protein isoform (from a non-reduced or a reduced sample portion) and the standardized fluorescent signal associated with the known quantity of free thiol groups. In some instances, a quantity of disulfide groups in the sample can be measured based on a difference between the absolute quantity of total thiol groups and the absolute quantity of free thiol groups measured in a sample. For example, the additional number of thiol groups in the total thiol groups above the free thiol groups can be attributed to the disulfide groups that were reduced by the application of a reducing agent.

As described herein, the systems and methods disclosed can be used to determine, in a protein isoform specific manner, a quantity of free thiol groups in a sample containing protein isoforms. Further, by using a reducing agent, the systems and methods disclosed can be used to determine, also in a protein isoform specific manner, a quantity of total thiol and/or a quantity of disulfide groups included in the protein isoforms contained in the sample. In some instances, the quantified thiol groups and/or disulfide groups can be surface thiols or surface disulfides. In some implementations, the systems and methods described herein can be used to determine, also in a protein isoform specific manner, a quantity of internal thiol groups and/or internal disulfide groups in a protein isoform.

In some instances, a protein isoform can assume a three dimensional structure, for example, according to a conformational state of the protein isoform. Based on the three dimensional structure, some of the thiol groups and/or disulfide groups included in the protein isoform can be accessible surface thiol groups and/or surface disulfide groups. Some other thiol groups and/or disulfide groups may be internal thiol groups and/or disulfide groups, hidden, unexposed and/or inaccessible by detection binders due to the three dimensional structure or conformation of the protein isoform. In some implementations, the systems and methods described herein can be used to detect and/or quantify these internal or hidden thiols groups and/or disulfide groups by denaturing the protein isoform and converting the hidden internal thiol groups into free thiol groups accessible to detection binders. Following the denaturing, for example by applying urea or any other suitable denaturing agent, the systems and methods described herein can be used to determine a quantity of free thiol groups as described previously (e.g., with reference to method 200 and/or method 300 described above).

In some implementations, determination of a quantity of free thiol groups before and after denaturing can be used to calculate a quantity of internal thiol groups. For example, a difference between the quantity of free thiol after denaturing and the quantity of free thiol groups before denaturing can be used to obtain a quantity of internal thiol groups). In some implementations, a number of free thiols groups and a number of internal thiol groups can be quantified and based on a determination of a quantity of each protein isoform, a quantity of free thiols groups and a quantity of hidden thiol groups can be determined. In some implementations, a combination of applying a reducing agent and a denaturing agent can be used to quantify a quantity of free surface thiol groups, surface disulfide groups, internal thiol groups, and/or internal disulfide groups. For example, a first reducing agent and a denaturing agent and a second reducing agent can be sequentially applied to a sample containing protein isoforms, such that the number of free thiol groups is incrementally and/or cumulatively increased by the reducing and the denaturing steps. In some implementations, the first reducing agent can be configured to convert surface disulfide groups into free thiol groups. The denaturing agent can be configured to make internal free thiol groups accessible to be conjugated with detection binders and/or make internal disulfide groups accessible to a reducing agent. The second reducing agent (which in some implementations can be a reapplication of the same reducing agent as the first reducing agent) can be configured to convert the now accessible disulfide groups, which were inaccessible before the denaturing, into free thiol groups. From determining a quantity of free thiol groups before and after applying the reducing agent, determining a quantity of free thiol groups before and after applying the denaturing agent, determining a quantity of free thiol groups before and after applying the second reducing agent, and calculating differences between each determined quantity of free thiol groups and the quantity of free thiol prior to each manipulation, one can calculate a quantity of surface free thiol groups, surface disulfide groups, internal thiol groups and/or internal disulfide groups. As an example, a difference between the quantity of free thiol after denaturing and the quantity of free thiol groups before denaturing can be used to obtain a quantity of internal thiol groups. In some implementations, the denaturing can be carried in out in one or more steps using any suitable method (e.g., chemical denaturing agent, heat based denaturing, pH based denaturing, etc).

Figure 4:
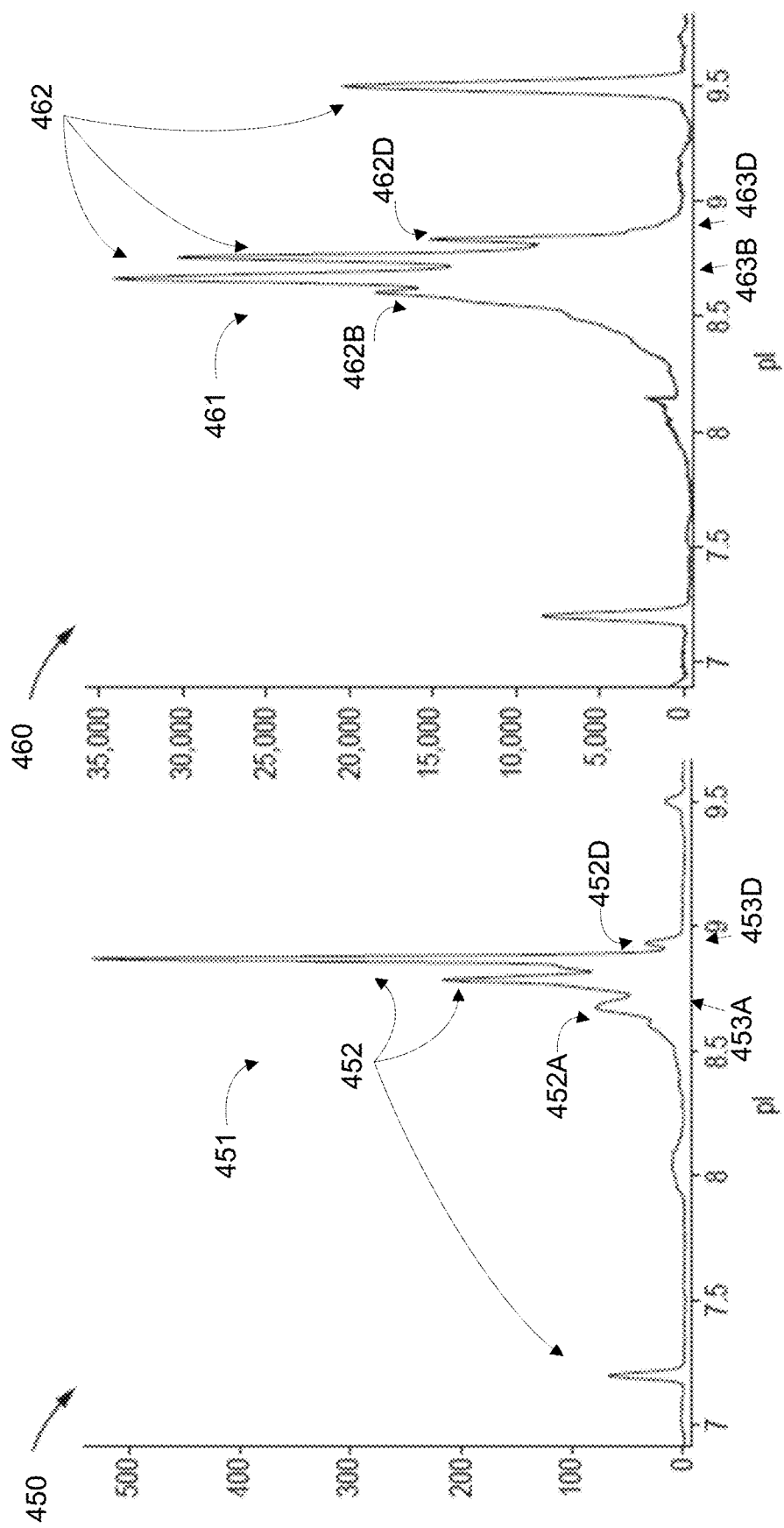
FIG. 4A is a chart showing a plot of an example absorbance signal detected from a sample containing a plurality of proteins and/or protein isoforms, plotted as a function of isoelectric point, using a system as described herein, according to an embodiment.
FIG. 4B is a chart showing a plot of an example fluorescence signal detected from the sample containing a plurality of proteins and/or protein isoforms shown in FIG. 4A, plotted as a function of isoelectric point, using a system as described herein, according to an embodiment.

FIGS. 4A and 4B illustrate a charts 450 and 460 showing plots of an example absorbance signal 451 and an example fluorescence signal 461 obtained from a Herceptin® Biosimilar sample, which contains a plurality of proteins and/or protein isoforms including therapeutic proteins, using a system as described herein, according to an embodiment. The plurality of proteins and/or protein isoforms in the sample associated with the absorbance signal 451 and the fluorescence signal 461 can be separated using imaged capillary isoelectric focusing over a pH gradient. The absorbance signal 451 of FIG. 4A is shown to be plotted as a measure of intensity of absorbance (measured in mAU—milli absorbance units) as a function of isoelectric poing (pI). The fluorescence signal 461 of FIG. 4B is shown to be plotted as a measure of intensity of fluorescence emission (measured in arbitrary counts) as a function of isoelectirc point (pI).

As shown in FIG. 4A, the absorbance signal 451 includes peaks 452 with each peak corresponding to a protein isoform (or pI marker, at pI 7.2) having the corresponding pI value. As an example, a relatively larger peak 452A of absorbance is associated with a protein isoform A with a pI of approximately 8.65 at 453A compared to a relatively smaller peak 452D of absorbance that is associated with a protein isoform D with a pI of approximately 8.9 at 453D. The measurement of the absorbance signal 451 at a given pI value corresponding to a specific protein isoform can be used to determine a relative quantity of that specific protein isoform. The differential absorbance between the peaks 452A and 452D can indicate a difference in the constituent amino acids included in the protein isoform A and the protein isoform D. For example, the differential absorbance can arise from a difference in the specific amino acids (e.g., amino acids with charged side chains and/or chemical changes to the charged side chains such as deamidation, glycation, or the like) included in the separated protein isoform A compared to the separated protein isoform B.

As shown in FIG. 4B, the fluorescence signal 461 includes peaks 462 with each peak corresponding to each separated protein isoform having the corresponding pI value. As an example, a relatively larger peak 462B of fluorescence is associated with a protein isoform B with a pI of approximately 8.75 at 463B compared to a relatively smaller peak 462D of fluorescence that is associated with the protein isoform D with a pI of approximately 8.9 at 463D. The differential fluorescence between the peaks 462B and 462D can indicate a difference in the amount of free thiol groups included in the protein isoform B and the protein isoform D. As described previously, control markers or pI markers can be used, for example to calibrate the method used for separation of protein isoforms, by generating peaks at known pI values as true positives. For example, the peak of absorbance at pI values 7.2 in the absorbance signal 451 and the peak of fluorescence at pI values 7.2 in fluorescence signal 461 can correspond to a control marker or a pI marker.

Figure 5:
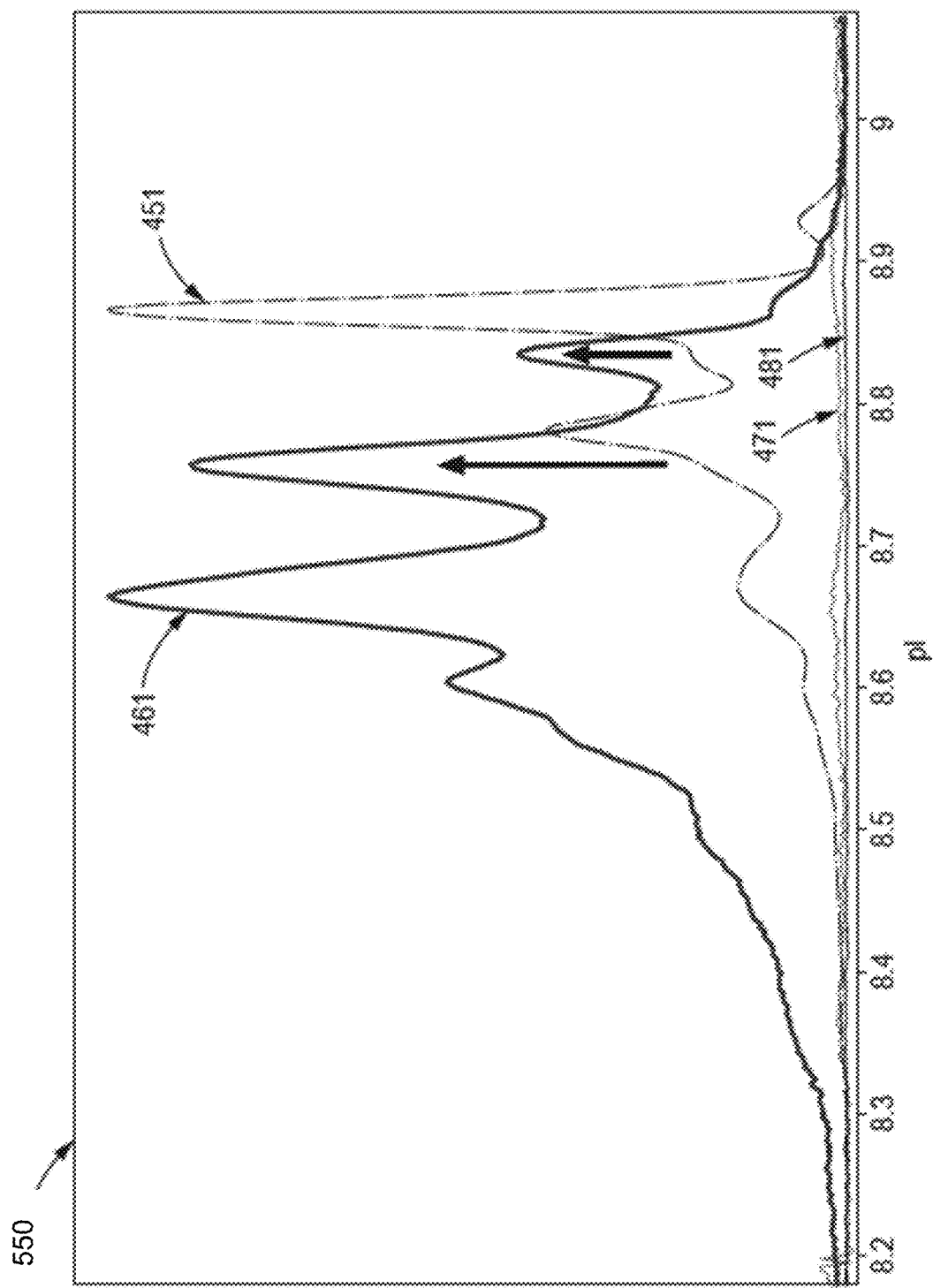
FIG. 5 is a chart showing an overlay of the absorbance signal of FIG. 4A and the fluorescence signal shown in FIG. 4B, indicating a relationship between peaks observed in each signal with the peaks observed in the other signal, the peaks being associated with a set of plurality of proteins and/or protein isoforms of the plurality of proteins and/or protein isoforms, as analyzed using a system as described herein, according to an embodiment.

FIG. 5 is a chart 550 showing an overlay of the absorbance signal 451 of FIG. 4A and the fluorescence signal 461 shown in FIG. 4B. The experimental examination of the Herceptin® Biosimilar sample described with reference to FIGS. 4A and 4B, also included examination of detection binders (e.g., fluorescent dyes) that were unbound or unconjugated with any protein isoforms, also referred to as "dye blank". In addition to detection and measurement of fluorescence and absorbance signals associated with protein isoforms, fluorescence and absorbance signals were also acquired from the dye blank or the detection binders (e.g., fluorescent dyes) that were unbound or unconjugated with any protein isoforms to be used as reference signals. FIG. 5 also includes example reference signals 471 and 481. The reference signal 471 corresponds to fluorescence signal acquired from detection binders unbound to any protein isoforms. The reference signal 481 corresponds to or an absorbance signal acquired from detection binders unbound to any protein isoforms. In some implementations, the examination of dye blank to acquire reference signals can be performed independently from the separation and examination of protein isoforms in a sample (e.g., in a separate run or session from the run or session involving separation and measurement of fluorescence and/or absorbance signals associated with protein isoforms). In some implementations, the examination of dye blank to acquire reference signals can be performed along with the separation and examination of protein isoforms in a sample, for example by allocating a separate track or capillary for the dye blank such that the dye blank is not exposed to protein isoforms.

As shown, the reference signal 471 lacks discernible peaks indicating that the peaks observed in the fluorescence signal 461 are truly associated with detection binders that are bound to protein isoforms and are not spurious signal artifacts. The reference signal 481 also is shown to lack specific peaks in intensity showing that the peaks observed in the absorbance signal 451 are truly absorbance associated with protein isoforms and not spurious absorbance artifacts. The plot of fluorescence signal 461 and absorbance signal 451 illustrate a relationship between peaks observed in each signal with the peaks observed in the other signal, the peaks being associated with a set of plurality of proteins and/or protein isoforms of the plurality of proteins and/or protein isoforms, as analyzed using a system as described herein, according to an embodiment. Two example pairs of peaks and their correspondence are indicated by arrows.

Free thiols can be used as a critical quality attribute of proteins (e.g., therapeutic proteins) to grade a quality associated with the protein. A critical quality attributes (CQA) of a clinical product can be defined as "A physical, chemical, biological, or microbiological property or characteristic that should be within an appropriate limit, range, or distribution to ensure the desired product quality" Said in another way products (e.g., therapeutics, monoclonal antibodies (mAbs), etc.) can have identified CQAs (e.g., as a part of implementation of quality by design (QbD) for development and production of biopharmaceuticals) that can include attributes that have an impact on the clinical efficacy and/or safety of the clinical product. An amount of free thiols in a product can be considered a CQA for product development. Free thiols can be a leading cause of aggregation, which can lead to immunogenicity, thus impacting efficacy. In some instances, free thiols can form during harvesting and/or purification process of a therapeutic protein. In some instances, for example, free thiols can be generated during the production of bispecific antibodies and/or Antibody Drug Conjugates (ADCs). Therefore amount of free thiols as determined by the method described herein using systems described herein can be used as a CQA for therapeutic proteins.

In some instances, the methods described herein can also be used to calculate ADC labeling efficiency measurements. In some instances, methods and systems described hereon can be used to quantify bi- and/or multi-specific antibody reassembly, for example, in conditions involving sulfhydryl group manipulation. Bi-specific antibodies are generated as individual half-antibodies, purified, then subsequently exposed to a mild reductant to reduce the hinge region to facilitate assembly of the complete (or whole) bi-specific antibody. The methods described herein allow quantitation of free-thiol pre- and post-assembly of bi- and multi-specific antibodies.

For example, the fluorescent detection binders used to bind with thiols can be a first set of fluorescent detection binders. Additionally, a second set of fluorescent detection binders can be used with a fluorescence emission in a band of wavelengths different from the band of wavelengths of light emitted by the first set of fluorescence detection binders. The second set of fluorescent detection binders can be configured to bind to a drug included in an ADC such that upon being excited by a light (e.g., a light of a single wavelength in the UV range (e.g., 280 nm)) (i) the emission from the first set of fluorescence detection binders can be used to quantify an amount of free thiols associated with the ADC included in each separated protein isoform of a set of separated protein isoforms, and (ii) the emission from the second set of fluorescence detection binders can be used to measure an antibody-to-drug ratio associated with the ADC included in each separated protein isoform of a set of separated protein isoforms. In some implementations, the systems and/or methods described herein can be used to perform secondary measurements or assessments in addition to the quantification of free and/or total thiol quantification. For example, as the fluorescent detection binders can be configured to have no effect or have a controlled effect on the charge heterogeneity of protein isoforms included in a sample, such that the effect can be accounted for, the methods used for quantification of thiol content (free and/or total thiol groups) also referred to as fluorescent thiol derivatization, may not affect the charge of the un-derivatized isoform. Thus, additional "shift assays" could be developed to further analyze the protein isoforms. The derivatization of mono-charged or multi-charged fluorescent dyes could be used isolate a CQA from the rest of sample peaks for baseline integration and quantification. The inclusion of additional charged entities to the labeling reagent could induce a significant shift that isolates the peaks of interest (labeled with dye) away from unlabeled overlapping protein isoform peaks.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the term "sample" refers to a composition that contains an analyte or analytes to be analyzed or detected or used otherwise. A sample can be heterogeneous, containing a variety of components (e.g., different proteins, different types of protein isoforms, different complexes or conjugates of components like antibody drug conjugates or other components conjugated with proteins etc.) or homogenous, containing one component. In some instances, a sample can be naturally occurring, a biological material, and/or a man-made material. Furthermore, a sample can be in a native or denatured form. In some instances, a sample can be a single cell (or contents of a single cell) or multiple cells (or contents of multiple cells), a blood sample, a plasma sample, a tissue sample, a skin sample, a urine sample, a water sample, etc. In some instances, a sample can be from a living organism, such as a eukaryote, prokaryote, mammal, and/or human.

Devices and/or systems disclosed herein can include any suitable electronic devices. For example, in some embodiments, instruments can include an integral compute device and/or a peripheral compute device such as a personal computer (PC), a personal digital assistant (PDA), a smart phone, a laptop, a tablet PC, a server device, a workstation, and/or the like. The compute device can include at least a memory, a processor. In some embodiments, the compute device can an output device, which can be any suitable display that can provide at least a portion of a user interface for a software application (e.g., a mobile application, a PC application, an internet web browser, etc.) installed on the electronic device. In such embodiments, the display can be, for example, a cathode ray tube (CRT) monitor, a liquid crystal display (LCD) monitor, a light emitting diode (LED) monitor, and/or the like. In other embodiments, the output device can be an audio device, a haptic device, and/or any other suitable output device. In some embodiments, the compute device can include a network interface, which can be, for example, a network interface card and/or the like that can include at least an Ethernet port and/or a wireless radio (e.g., a WiFi® radio, a Bluetooth® radio, etc.). The memory can be, for example, a random access memory (RAM), a memory buffer, a hard drive, a read-only memory (ROM), an erasable programmable read-only memory (EPROM), and/or the like. The processor can be any suitable processing device configured to run or execute a set of instructions or code. For example, the processor can be a general purpose processor, a central processing unit (CPU), an accelerated processing unit (APU), and Application Specific Integrated Circuit (ASIC), and/or the like. The processor can be configured to run or execute a set of instructions or code stored in the memory associated with using, for example, a PC application, a mobile application, an internet web browser, a cellular and/or wireless communication (via a network), and/or the like, as described in further detail herein. The memory can be, for example, a random access memory (RAM), a memory buffer, a hard drive, a read-only memory (ROM), an erasable programmable read-only memory (EPROM), cloud storage and/or the like. In some embodiments, the memory can be configured to store, for example, one or more modules that can include instructions that can cause a processor to perform one or more processes, functions, and/or the like.

While various embodiments have been described herein, it should be understood that they have been presented by way of example only, and not limitation. For example, although embodiments described herein involve proteins and/or protein isoforms, it should be understood that methods described herein are also applicable to other thiol-containing materials. Furthermore, although various embodiments have been described as having particular features and/or combinations of components, other embodiments are possible having a combination of any features and/or components.

While various embodiments have been described above, it should be understood that they have been presented by way of example only, and not limitation. Where methods and steps described above indicate certain events occurring in certain order, the ordering of certain steps may be modified. In some instances, certain steps may be followed while certain other steps may be omitted. For example, although some embodiments are described carrying out fluorescence emission measurements and/or absorbance measurements on a first portion of a sample containing a detection binder and carrying out fluorescence emission measurements and/or absorbance measurements on a second portion of the sample that does not contain detection binders, it should be understood that in other embodiments, the sample may not be divided into two portions, a detection binder can be added to the sample, and fluorescence emission measurements and/or absorbance measurements may be carried out only on the sample containing the detection binder. As another example, in some instances fluorescence emission measurements can be carried while omitting UV absorbance measurements or vice versa. Additionally, certain of the events may be performed repeatedly, concurrently in a parallel process when possible, as well as performed sequentially as described above. For example, detecting fluorescence in a sample well is described before detecting UV absorbance is described. It should be understood, however, that detecting fluorescence and UV absorbance can occur in any order or simultaneously. Furthermore, certain embodiments may omit one or more described events.

Where methods are described, it should be understood that such methods can be computer-implemented methods. Similarly stated, a non-transitory processor readable medium can store code representing instructions configured to cause a processor to cause the described method to occur or be carried out. For example, an instrument, such as Maurice™ produced and sold by ProteinSimple®, a Bio-Techne® brand, can include a processor and a memory and can cause one or more method steps described herein to occur. Thus, some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes.

Although various embodiments have been described as having particular features and/or combinations of components, other embodiments are possible having any combination or sub-combination of any features and/or components from any of the embodiments described herein.

The invention claimed is:

1. A method, comprising:
separating a plurality of protein isoforms in a first portion of a sample to generate a first set of separated protein isoforms, the first portion of the sample containing a detection binder that binds to free thiols to form conjugated thiols;
detecting a first fluorescence signal associated with conjugated thiols in the first set of separated protein isoforms;
separating a plurality of protein isoforms in a second portion of the sample to generate a second set of separated protein isoforms;
detecting a second fluorescence signal associated with the second set of separated protein isoforms; and
measuring, based on a difference between the first fluorescence signal and the second fluorescence signal, a quantity of free thiol groups associated with each separated protein isoform from the first set of separated protein isoforms.

2. The method of claim 1, further comprising preparing the sample, including dividing the sample into the first portion and the second portion.

3. The method of claim 1, wherein the detection binders are configured such that they bind to free thiols without reducing the plurality of protein isoforms.

4. The method of claim 1, wherein separating the plurality of protein isoforms in the first portion of the sample and separating the plurality of protein isoforms in the second portion of the sample occur in parallel.

5. The method of claim 1, wherein separating the plurality of protein isoforms in the first portion of the sample occurs before separating the plurality of protein isoforms in the second portion of the sample.

6. The method of claim 1, wherein separating the plurality of protein isoforms in the second portion of the sample occurs before separating the plurality of protein isoforms in the first portion of the sample.

7. The method of claim 1, wherein the detection binder is a first detection binder, the method further comprising:
reducing disulfide bonds in a third portion of the sample;
separating the plurality of protein isoforms in the third portion of the sample to generate a third set of separated protein isoforms, the third portion of the sample containing a second detection binder that binds to thiol groups, including thiol groups formed by reducing disulfide bonds;
detecting a third fluorescence signal associated with conjugated thiols in the third set of separated protein isoforms; and
measuring a total thiol content in the sample based on a difference in the third fluorescence signal and the first fluorescence signal.

8. The method of claim 7, wherein the first detection binder and the second detection binder are the same detection binder.

9. The method of claim 1, wherein the detection binder is a first detection binder, the method further comprising:
reducing disulfide bonds in a third portion of the sample;
separating the plurality of protein isoforms in the third portion of the sample to generate a third set of separated protein isoforms, the third portion of the sample containing a second detection binder that binds to thiol groups, including thiol groups formed by reducing disulfide bonds;
detecting a third fluorescence signal associated with conjugated thiols in the third set of separated protein isoforms; and
measuring a quantity of disulfide bonds in the sample based on a difference in the third fluorescence signal and the first fluorescence signal.

10. The method of claim 1, further comprising:
reducing disulfide bonds in the first portion of the sample after detecting the first fluorescence signal;
detecting a third fluorescence signal associated with conjugated thiols, including thiols formed by reducing disulfide bonds; and
measuring a quantity of disulfide bonds in the sample based on a difference in the third fluorescence signal and the first fluorescence signal.

11. The method of claim 1, further comprising:
measuring an absorbance associated with the first set of separated protein isoforms; and
identifying at least one of a quantity or an identity of the at least one separated protein isoform from the first set of separated protein isoforms based on the absorbance, wherein measuring the quantity of free thiol groups includes identifying a quantity of free thiol groups associated with the at least one separated protein isoforms.

12. A method, comprising:
separating a plurality of protein isoforms in a first portion of a sample to generate a first set of separated protein isoforms;
introducing a detection binder configured to bind to free thiols to form conjugated thiols after separating the plurality of protein isoforms in the first portion of the sample;
detecting a first fluorescence signal associated with conjugated thiols in the first set of separated protein isoforms;
separating a plurality of protein isoforms in a second portion of the sample to generate a second set of separated protein isoforms;
detecting a second fluorescence signal associated with the second set of separated protein isoforms; and
measuring, based on a difference between the first fluorescence signal and the second fluorescence signal, a quantity of free thiol groups associated with each separated protein isoform from the first set of separated protein isoforms.

13. The method of claim 12, further comprising:
measuring an absorbance associated with the first set of separated protein isoform; and
identifying at least one of a quantity or an identity of the at least one separated protein isoform from the first set of separated protein isoforms based on the absorbance, wherein measuring the quantity of free thiol groups includes identifying a quantity of free thiol groups associated with the at least one separated protein isoforms.

14. A method, comprising:
separating a plurality of protein isoforms in a sample to generate a set of separated protein isoforms, the sample containing detection binders that bind to free thiols to form conjugated thiols;
detecting a fluorescence signal associated with conjugated thiols for at least one separated protein isoform from the set of separated protein isoforms;
measuring an absorbance of at least one separated protein isoform from the set of separated protein isoforms;
identifying at least one of a quantity or an identity of the at least one separated protein isoform from the plurality of separated protein isoforms based on the absorbance; and
determining a quantity of free thiol groups associated with the at least one separated protein isoform based on the fluorescence signal.

15. The method of claim 14, wherein:
detecting the fluorescence signal includes detecting a fluorescence signal associated with conjugated thiols for a plurality of protein isoforms from the set of separated protein isoforms;
measuring the absorbance includes measuring the absorbance of the plurality of separated protein isoforms;
identifying at least one of the quantity or the identity includes identifying at least one of the quantity or the identity of each separated protein isoform from the plurality of separated protein isoforms; and
determining the quantity includes determining the quantity of free thiol groups associated with the plurality of separated protein isoforms.

16. The method of claim 14, wherein:
separating the plurality of protein isoforms includes separating a first portion of the sample to generate a first set of separated protein isoforms; and
detecting the fluorescence signal includes detecting a first fluorescence signal, the method further comprising:
separating the plurality of protein isoforms in a second portion of the sample to generate a second set of separated protein isoforms;
detecting a second fluorescence signal associated with the second set of separated protein isoforms; and
measuring, based on a difference between the first fluorescence signal and the second fluorescence signal, a quantity of free thiol groups associated with the at least one separated protein isoform.

17. The method of claim 14, wherein:
separating the plurality of protein isoforms includes separating a first portion of the sample to generate a first set of separated protein isoforms;
detecting the fluorescence signal includes detecting a first fluorescence signal; and
measuring the absorbance includes measuring a first absorbance, the method further comprising:
separating the plurality of protein isoforms in a second portion of the sample to generate a second set of separated protein isoforms;
detecting a second fluorescence signal associated with the second set of separated protein isoforms;
measuring a second absorbance of the at least one protein isoform from the second set of separated protein isoforms; and
determining a relative amount of the at least one protein isoform based on a difference between the first absorbance and the second absorbance.

18. The method of claim 17, wherein detection binders are configured such that they bind to free thiols without reducing the plurality of protein isoforms.

19. The method of claim 14, wherein detection binders are configured such that they bind to free thiols without reducing the plurality of protein isoforms, the method further comprising:
separating the plurality of protein isoforms includes separating a first portion of the sample to generate a first set of separated protein isoforms;
detecting the fluorescence signal includes detecting a first fluorescence signal; and
measuring the absorbance includes measuring a first absorbance, the method further comprising:
reducing disulfide bonds in the plurality of protein isoforms in a second portion of the sample;
separating the plurality of protein isoforms in the second portion of the sample to generate a second set of separated protein isoforms;
detecting a second fluorescence signal associated with the second set of separated protein isoforms after reducing disulfide bonds in the second portion of the sample; and
determining a total thiol content associated with the at least one separated protein isoform based on a difference in the second fluorescence signal and the first fluorescence signal.

20. The method of claim 14, wherein detection binders are configured such that they bind to free thiols without reducing the plurality of protein isoforms, the method further comprising:
separating the plurality of protein isoforms includes separating a first portion of the sample to generate a first set of separated protein isoforms;

detecting the fluorescence signal includes detecting a first fluorescence signal; and measuring the absorbance includes measuring a first absorbance, the method further comprising:

reducing disulfide bonds in the plurality of protein isoforms in a second portion of the sample;

separating the plurality of protein isoforms in the second portion of the sample to generate a second set of separated protein isoforms;

detecting a second fluorescence signal associated with the second set of separated protein isoforms after reducing disulfide bonds in the second portion of the sample; and determining a total thiol content in the sample based on a difference in the second fluorescence signal and the first fluorescence signal.

21. The method of claim 14, wherein the fluorescence signal is obtained simultaneously with measuring the absorbance.

* * * * *